United States Patent [19]
Zurawski et al.

[11] Patent Number: 5,696,234
[45] Date of Patent: Dec. 9, 1997

[54] MUTEINS OF MAMMALIAN CYTOKINE INTERLEUKIN-13

[75] Inventors: Sandra M. Zurawski; Gerard Zurawski, both of Redwood City, Calif.

[73] Assignee: Schering Corporation, Kenilworth, N.J.

[21] Appl. No.: 284,393

[22] Filed: Aug. 1, 1994

[51] Int. Cl.$^6$ .......................... C07K 14/54; A61K 38/20
[52] U.S. Cl. .......................... 530/351; 435/69.52; 514/2; 514/12; 424/85.2
[58] Field of Search .......................... 435/69.52; 514/2, 514/12; 530/350, 351; 424/85.2

[56] References Cited

U.S. PATENT DOCUMENTS 5,229,109  7/1993  Grimm et al. .......................... 424/85.2

FOREIGN PATENT DOCUMENTS

WO 90/00565  1/1990  WIPO .

OTHER PUBLICATIONS

Brown et al. (1989). J. of Immunology. vol. 142, pp. 679–687.
Schulz et al. "Principles of Protein Structure", published 1979 by Springer–Verlag N.Y. Inc., pp. 14–16.
Bowie et al. (1990) Science, vol. 247 pp. 1306–1310.
Ken-ichi Arai, et al., "Cytokines: Coordinators of Immune and Inflammatory Responses," *Ann. Rev. Biochem.* 59:783–836, 1990.
Gian Carlo Avanzi, et al., "Selective Growth Response to IL–3 of a Human Leukaemic Cell Line with Megakaryoblastic Features," *Br. J. Haematol.* 69:359–366, 1988.
Just P.J. Brakenhoff, et al., "Development of a Human Interleukin–6 Receptor Antagonist," *J. Biol. Chem.* 269(1):86–93, Jan. 7, 1994.
Takashi Fujita, et al., "Structure of the Human Interleukin 2 Gene," *Proc. Nat'l. Acad. Sci.* 80:7437–7441, Dec. 12 1983.
M.C. Fung "Molecular Cloning of cDNA for Murine Interleukin–3," *Nature* 307:233–237, Jan. 1994.
Steven Gillis, et al., "T Cell Growth Factor: Parameters of Production and a Quantitative Microassay for Activity," *J. Immunol.* 120(6):2027–2032, Jun. 1978.
Nicholas Gough, et al., "Molecular Cloning of cDNA Encoding a Murine Haematopoietic Growth Regulator, Granulocyte–Macrophage Colony Stimulating Factor," 309:763–767, Jun. 1984.
Kenneth H. Grabstein, et al., "Cloning of T Cell Growth Factor That Interacts with the βChain of the Interleukin–2 Receptor,"*Science*, 264:965–968, May 13, 1994.
Kevin L. Holmes, et al., "Correlation of Cell–Surface Phenotype with the Establishment of Interleukin 3–Dependent Cell Lines from Wild–Mouse Murine Leukemia Virus Induced Neoplasms," *Proc. Nat'l. Acad. Sci.* 82:6687–6691, Oct. 1985.
Maureen Howard, et al., "B Cell Growth and Differentiation Factors," *Immunol. Rev.* 78:185–210, 1984.

Jean–Luc Imler, et al., "Identification of Three Adjacent Amino Acids of Interleukin–2 Receptor β Chain which Control the Affinity and the Specificity of the Interaction with Interleukin–2," *The EMBO J.* 11(6):2047–2053, 1992.
Kenji Izuhara, et al., "The Chimeric Receptor between Interleukin–2 Receptor β Chain and Interleukin–4 Receptor Transduces Interleukin–2 Signal," *Biochem. Biophys. Res. Comm.* 190(3):992–1000, Feb. 15, 1993.
Tatsuo Kinashi, et al., "Cloning of Complementary DNA Encoding T–Cell Replacing Factor and Identity with B–Cell Growth Factor II," *Nature* 324:70–73, Nov. 6, 1986.
N. Kruse, et al., "Conversion of Human Interleukin–4 into a High Affinity Antagonist by a Single Amino Acid Replacement," *The EMBO J.* 11(9):3237–3244, 1992.
N. Kruse, et al., "Two Distinct Functional Sites of Human Interleukin 4 Are Identified by Variants Impaired in Either Receptor Binding or Receptor Activation," N. Kruse, et al., Two Distinct Functional Sites of Human Interleukin 4 Are Identified by Variants Impaired in Either Receptor Binding or Receptor Activation, *The EMBO J.* 12(13):5121–5129, 1993.
Beverly Lange, et al., "Growth Factor Requirements of Childhood Acute Leukemia: Establishment of GM–CS-F–Dependent Cell Lines," *Blood* 70:192–199, Jul. 1987.
Frank Lee, et al., "Isolation of cDNA for a Human Granulocyte–Macrophage Colony–Stimulating Factor by Functional by Functional Expression in Mammalian Cells," *Proc. Nat'l Acad. Sci.* 82:4360–4364, Jul. 1985.
Stephen D. Lupton, et al., "Characterization of the Human and Murine IL–7 Genes," *J. Immunol.* 144(9);3592–3601, May 1, 1990.
A.N.J. McKenzie, et al., "Interleukin–13, A T–Cell–Derived Cytokine That Regulates Human Monocyte and B–Cell Function," *Proc. Nat'l. Acad. Sci.* 90:3735–3739, Apr. 1993.
Anthony E. Namen et al., "Stimulation of B–Cell Progenitors by Cloned Murine Interleukin–7," *Nature* 333(9):571–573, Jun. 1988.
Jean–Christophe Renauld, et al., "Human P40/II–9: Expression in Activated CD4+ T Cells, Genomic Organization, and Comparison with the Mouse Gene," *J. Immunol.* 144(11):4235–4241, Jun. 1, 1990.
Robert S. Schwartz, et al., "Heavy–Chain Directed B–Cell Maturation: Continuous Clonal Selection Beginning at the Pre–B Cell Stage," *Immunol. Today* 15(1):27–31, 1994.
Armen Shanafelt, et al., "High Affinity Ligand Binding Is Not Essential for Granulocyte–Macrophage Colony–Stimulating Factor Receptor Activation," *J. Biol. Chem.* 267(35):25466–25472, Dec. 15, 1992.

(List continued on next page.)

*Primary Examiner*—John Ulm
*Assistant Examiner*—Prema Mertz
*Attorney, Agent, or Firm*—Edwin P. Ching; Sheela Mohan-Peterson

[57] ABSTRACT

Methods for screening for partial agonists and for antagonists of mammalian cytokines. Particular positions of natural cytokines are identified as critical in providing these receptor mediated properties. Specific embodiments demonstrate properties of variations at these positions.

11 Claims, 4 Drawing Sheets

OTHER PUBLICATIONS

Tetsuo Sudo, et al., "Interleukin 7 Production and Function in Stromal cell–Dependent B Cell Development," *J. Exp. Med.* 170:333–338, Jul. 1989.

Hergen Spits, et al., "Recombinant Interleukin 4 Promotes the Growth of Human T Cells," *J. Immunol.* 139(4):1142–1147, Aug. 15, 1987.

Jacques Van Snick, et al., "Cloning and Characterization of a cDNA for a New Mouse T Cell Growth Factor (P40),"*J. Exp. Med.* 169:363–368, Jan. 1989.

G.G. Wong, et al., "Molecular Cloning of Human and Gibbon T–Cell–Derived GM–CSF cDNAs and Purification of the Natural and Recombinant Human Proteins," *Cancer Cells* 3:235–242, 1985.

Yu–Chang Yang, et al., "Expression Cloning of a cDNA Encoding a Novel Human Hematopoietic Growth Factor: Human Homologue of Murine T–Cell Growth Factor P40," *Blood* 74(6):1880–1884, Nov. 1,1989.

Yu–Chang Yang, et al., "Human IL–3 (Multi–CSF): Identification by Expression Cloning of a Novel Hematopoietic Growth Factor Related to Murine IL–3," *Cell* 47:3–10, Oct. 10, 1986.

Junji Yodoi, et al., "TCGF (IL–2)–Receptor Inducing Factor(s): I Regulation of IL–2 Receptor on a Natural Killer–like Cell Line (YT Cells)," *J. Immunol.* 134(3):1623–1630, Mar. 1985.

Takashi Yokota, et al., "Isolation and Characterization of a Human Interleukin cDNA clone, homologous to Mouse B–Cell Stimulatory Factor 1, That Expresses B–Cell–and T–Cell–Stimulating Activities," *Proc. Nat'l, Acad, Sci.* 83:5894–5989, Aug. 1986.

Sandra M. Zurawski, et al., "Alterations in the Amino–Terminal Third of Mouse Interleukin 2: Effects on Biological Activity and Immunoreactivity," *J. Immunol.* 137:3354–3360, Nov. 15, 1986.

J. Fernando Bazan & David B. McKay, "Unraveling the Structure of IL–2," *Science*, 257:410–413, Jul. 1992.

Joachim F. Ernst, et al. "Screening of Muteins Secreted by Yeast: Random Mutagenesis of Human Interleukin–2," *Bio/Technology*, 7:716–720, Jul. 1989.

Grace Ju, et al. "Structure–Function Analysis of Human Interleukin–2: Idenditification of Amino Acid Residues Required for Biological Ativity," *J. of Biol. Chem.*, 262:5723–5731, 1987.

Bryan Landgraf, et al. "Structural Significance of the C–Terminal Amphiphilic Helix of Interleukin–2," *J. of Biol. Chem.*, 264:816–822, 1989.

Bryan Landgraf, et al. "Conformational Perturbation of Interleukin–2: A Strategy for the Design of Cytokine Analogs,"*Proteins: Structure, Function, and Genetics*, 9:207–216, 1991.

Shu–Mei Liang, et al., "Studies of Structure–Activity Relationships of Human Interleukin–2," *J. of Biol. Chem.*, 251:334–337, 1986.

Ulrich Weigel, et al. "Mutant Proteins of Human Interleukin 2," *Eur. J. Biochem.*, 180:295–300, 1989.

Sandra Zurawski, et al. "Partial Agonist/Antagonist Mouse Interleukin–2 Proteins Indicate that a Third Component of the Receptor Complex Functions in Signal Transduction," *Embo J.*, 9:3899–3905, 1990.

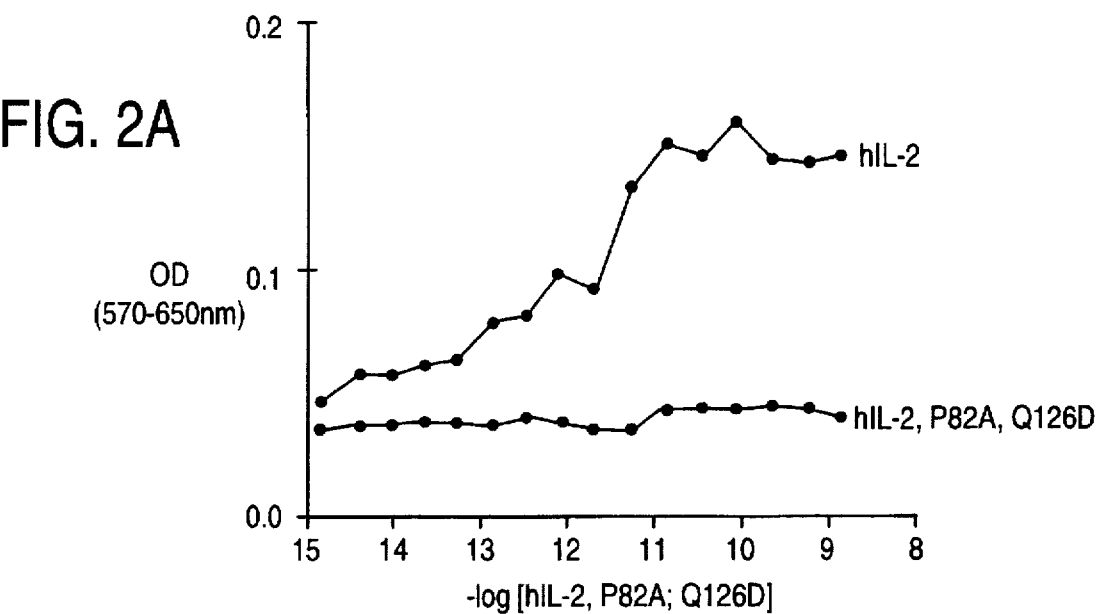
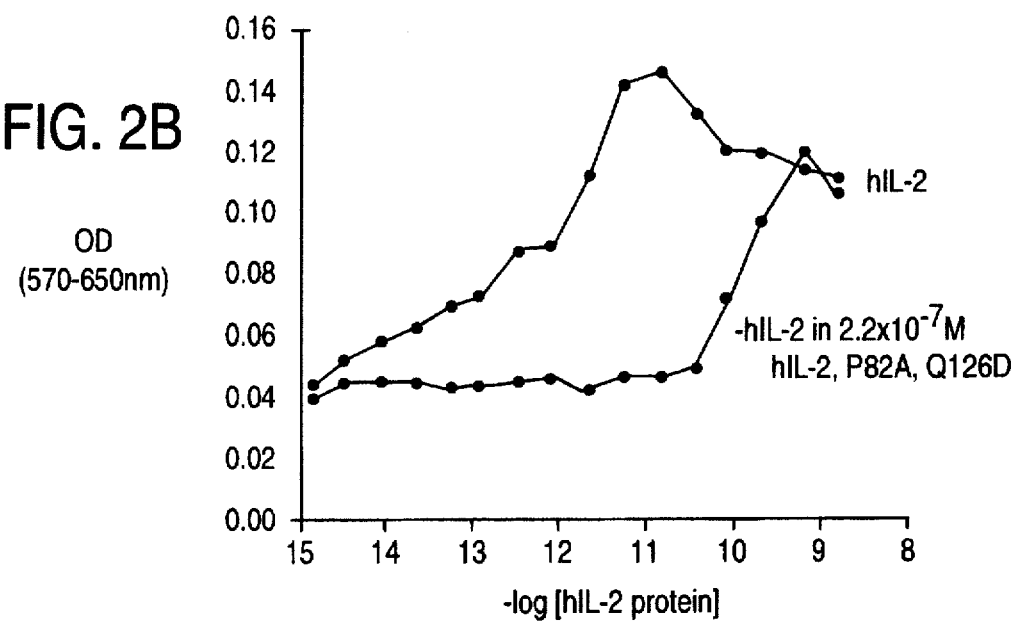

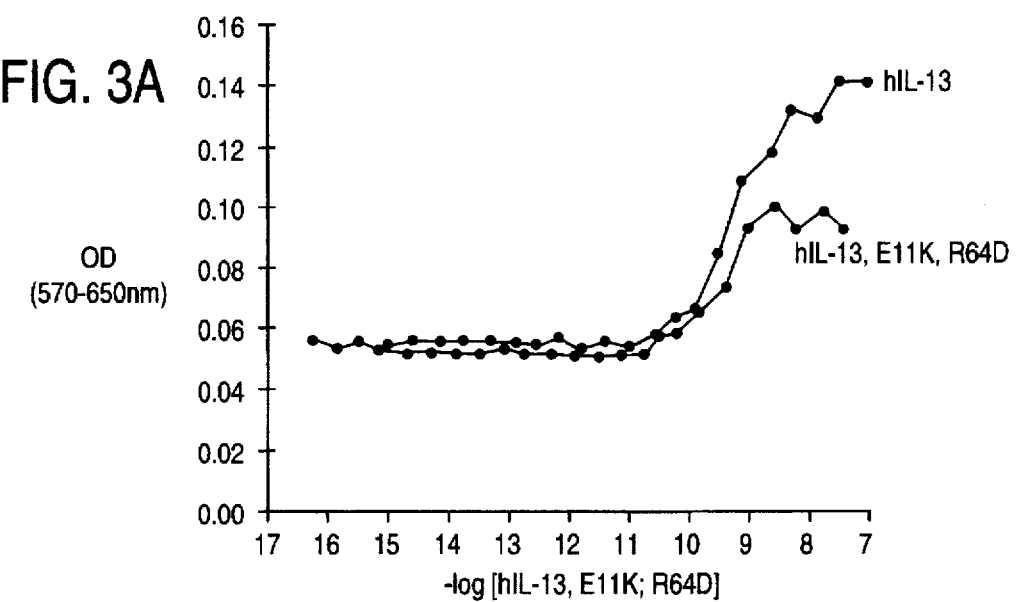
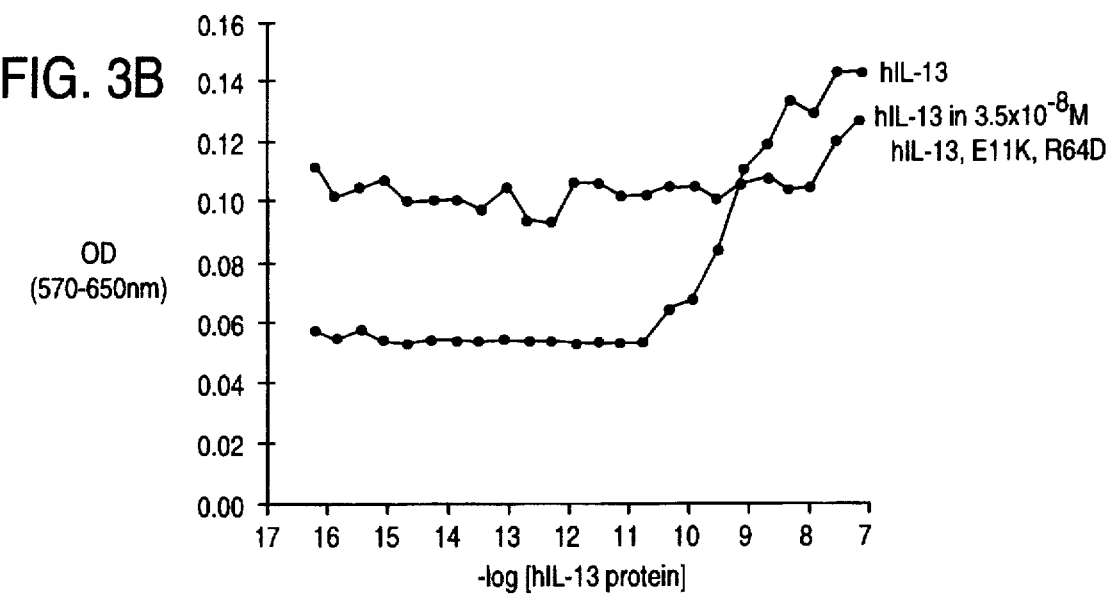

MUTEINS OF MAMMALIAN CYTOKINE INTERLEUKIN-13

FIELD OF THE INVENTION

The present invention relates to compositions which include variants of human cytokines which function in controlling development and differentiation of mammalian cells, e.g., cells of a mammalian immune system. In particular, it provides antagonists of proteins which regulate development, differentiation, and function of various cell types, including hematopoietic cells.

BACKGROUND OF THE INVENTION

The circulating component of the mammalian circulatory system comprises various cell types, including red and white blood cells of the erythroid or the myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.)(1993) *Fundamental Immunology* (3d ed.), Raven Press, N.Y. Myeloid cell production occurs through the differentiation and later commitment of myeloid progenitor cell lineages.

In addition, functional interaction of the various cell types involved in immune responses often involve transfer of signals via soluble messenger molecules. The cytokines and lymphokines are molecules which mediate differentiation or other signals, typically between cells. Cytokines function through receptors, many of which have been characterized. See, e.g., Aggarwal and Gutterman (eds.) (1991) *Human Cytokines;; Handbook for Basic and Clinical Research*, Blackwell, Oxford. As the cytokines are so important in development and regulation of immune responses, the inability to modulate these signals has prevented means to intervene in abnormal physiological or developmental situations. The present invention addresses these problems and provides various molecules which are useful in these situations.

SUMMARY OF THE INVENTION

The present invention provides molecules which can serve as an agonists or antagonist for various cytokines. These agonists and antagonists will be useful in diagnosis of cytokine or cytokine receptor levels. In certain circumstances, these molecules will also have in vitro or in vivo therapeutic effects.

The present invention is based, in part, upon the discovery of which specific amino acid residues of a cytokine are important in the binding and signal transduction components of cytokine-receptor binding. It embraces various mutein agonists and antagonists of the natural ligands, e.g., specific mutations (muteins) of the natural sequences, fusion proteins, and chemical mimetics. It is also directed to DNAs encoding such proteins. Various uses of these different protein or nucleic acid compositions are also provided.

The present invention provides a mutein of a human IL-2, said mutein exhibiting both:

1) partial cytokine agonist activity; and 2) a substitution in the sequence at a position:

a) between helix B and helix C; or b) in helix D.

In particular embodiments, the mutein has a sequence of:

| | |
|---|---|
| 1) | APTSSSTKKT QLQLEHLLLD LQMILNGINN YKNPKLTRML TFKFYMPKKA TELKHLQCLE EELKPLEEVL NLAQSKNFHL RpRDLISNIN VIVLELKGSE TIFMCEYADE TATIVEFLNR WITFCqSIIS TLT (SEQ ID NO: 1); |
| 2) | APTSSSTKKT QLQLEHLLLD LQMILNGINN YKNPKLTRML TFKFYMPKKA TELKHLQCLE EELKPLEEVL NLAQSKNFHL RpRDLISNIN VIVLELKGSE TIFMCETADE TATIVEFLNR WITFCqSIIS TLT (SEQ ID NO: 2); or |
| 3) | APTSSSTKKT QLQLEHLLLD LQMILNGINN YKNPKLTRML TFKFYMPKKA TELKHLQCLE EELKPLEEVL NLAQSKNFHL RpRDLISNIN VIVLELKGSE TIFMCETADE TATIVEFLNR WITFsqSIIS TLT (SEQ ID NO: 3). |

The mutein can also exhibit less than 80% maximal agonists activity of natural IL-2; and/or at a 1000-fold excess antagonizes cytokine agonist activity by at least about 50%. In particular embodiments, the mutein exhibits a substitution:

1) at a position between helix B and helix C which corresponds to position 82 (pro) of a hydrophobic amino acid, including alanine, and/or 2) at a position in helix D which corresponds to position 126 (gln) of an acidic amino acid, including aspartic acid.

The mutein can also contain substitutions at position 82 (pro and/or 126 (gln).

The invention also embraces a pharmaceutical composition comprising such mutein and a pharmaceutically acceptable carrier or excipient; a nucleic acid encoding these muteins; and methods of antagonizing biological activity of IL-2 on a cell comprising contacting the cell with such a mutein.

The invention also provides a mutein of a cytokine selected from:

1) a human IL-13, the mutein exhibiting both:

a) partial agonist activity; and b) a substitution in sequence at positions corresponding to:

i) a position in helix A; and/or ii) a position in helix C; and 2 a mouse P600, the mutein exhibiting both:

a) partial agonist activity; and b) a substitution in sequence at a position in helix C.

In various embodiments, the human IL-13 has a sequence of:

i) GPNVPPSTALR eLIEELVNIT QNQKAPLCNG SMVWSINLTA GMYCAALESL
   INVSGCSAIE KTQrMLSGFC PHKVSAGQFS SLHVRDTKIE VAQFVKDLLL
   HLKKLFREGR FN (SEQ ID NO: 4); or
ii) GPVPPSTALR eLIEELVNIT QNQKAPLCNG SMVNSINLTA GMYCAALESL
    INVSGCSAIE KTQrMLSGFC PHKVSAG-FS SLHVRDTKIE VAQFVKDLLL
    HLKKLFREGR FN (SEQ ID NO: 5); or the mouse P600 has a sequence of GPVPRSVSLP LILKELIEEL VNITQDETPL CNGSMVWSVD
LAAGGFCNAV ALDSLTNISN CIYRTQrILH GLCNRKAPTT
VSSLPDTKIE VAHFITKLLS YTKQLFRHGP F (SEQ ID NO: 6)

Preferably, these muteins exhibit less than 80% maximal agonist activity; and/or at a 100-fold excess antagonizes cytokine activity by at least 50%. In various embodiments, the position of:

1) human IL-13 in:
   a) helix A corresponds to position 11 (gly); and/or
   b) helix C corresponds to position 64 (arg); or
2) mouse P600 in helix C corresponds to position 67 (arg).

In particular embodiments, the substitution of human IL-13 is:

a) an aminated amino acid, including lysine, at position 11 (gly); and/or
b) an acidic amino acid, including aspartic acid, at position 64 (arg); or the substitution of mouse P600 is an acidic amino acid, including aspartic acid, at position 67 (arg). The invention also encompasses a nucleic acid encoding these muteins; methods of antagonizing biological activity of IL-4 or IL-13 on a cell by contacting the cell with such muteins; and methods of analyzing human IL-13 or mouse P600 by measuring antagonistic activity of such muteins in an assay.

In yet another embodiment, the present invention provides a mutein of a mammalian cytokine selected from the group consisting of:

1) IL-7;
2) IL-9; and
3) IL-15;

said mutein exhibiting both:

1) partial agonists activity; and
2) a substitution in the sequence at a position corresponding to a position in:
   a) IL-7 or IL-9 in between helix B and helix C; and/or helix D; or
   b) IL-15 in helix A and/or helix C.

BRIEF DESCRIPTION OF THE DRAWINGS

FIG. 1A shows antagonist activity of mouse IL-2 mutein Q141D. Abscissa: –log [mIL-2.Q141D] in Molar units; ordinate: OD (570–650 nm). The $I_{50}=2\times10^{-9}$ M. Assays used 100 μl per well, $10^4$ cells per well. FIG. 1B shows partial agonists activities on HT2 cells of various muteins of mouse iL-2, in particular, native, Q141K, Q141V, Q141L, and Q141D. Abscissa: –log [mIL-2 protein] in Molar units; ordinate: OD (570–650 nm). Positions corresponding D34, N99, and N103 in human IL-2 are predicted to be important. Similarly, in human IL-4, R88 (within the sequence of KDTRCLG) should be important.

FIGS. 2A–2B show partial agonist and antagonist activity of human IL-2 mutein P82A;Q126D on mouse Baf3 cells (see Imler, et al. (1992) *EMBO J*, 11:2047–2053). FIG 2A shows almost complete lack of agonist activity on mouse Baf3 cells cotransfected with both the α and β subunits of the human IL-2 receptor (see Izuhara, et al. *Biochem. Biophys. Res. Comm.* 190:992–1000). Abscissa: –log [hIL-2.P82A;Q126D] in Molar units; ordinate: OD (570–650 nm). FIG. 2B shows dose response curve of human IL-2 in the absence or presence of $2\times10^{-7}$ M IL-2 mutein. Abscissa: –log [hIL-2 protein] in Molar units; ordinate: OD (570–650 nm). Other important target residues in the human IL-2 include L94 and E95.

FIGS. 3A–3B show partial agonist and antagonist activity of human IL-13 mutein E11K;R64D on TF-1 cells. FIG. 3A shows partial agonist activity of this hIL-13 mutein. Abscissa: –log [hIL-13.E11K;R64D] in Molar units; ordinate: OD (570–650 nm). FIG. 3B shows dose response curve of human IL-13 in the absence or presence of $5\times10^{-8}$ M IL-13 mutein. Abscissa: –log [hIL-13 protein] in Molar units; ordinate: OD (570–650 nm). Position K61 of human IL-13 may also be important.

FIG. 4A shows partial agonist activity of mouse IL-13 mutein R67D on B9 cells. Abscissa: –log [mIL-13.R67D] in Molar units; ordinate: OD (570–650 nm). FIG. 4B shows dose response curve of mouse IL-13 in the absence or presence of $5\times10^{-7}$ M IL-13 mutein. Abscissa: –log [mIL-13 protein] in Molar units; ordinate: OD (570–650 nm).

Figure 1A:
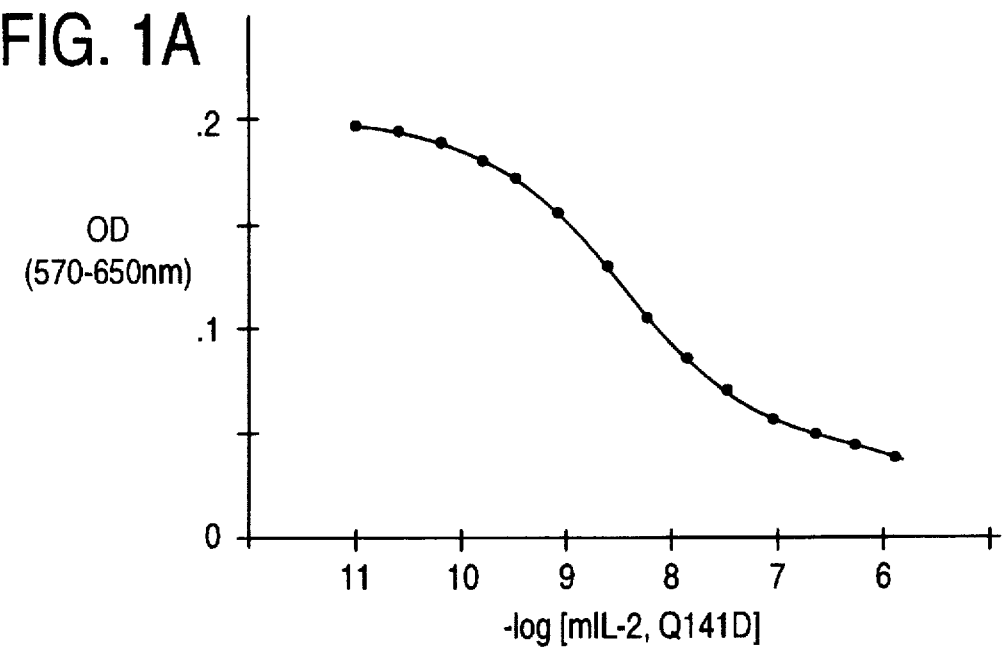
FIGS 1A–1B show effects of various muteins of mouse IL-2 on HT2 cells (see Zurawski, et al. (1986) *J. Immunol.* 137:3354–3360).
Figure 1B:
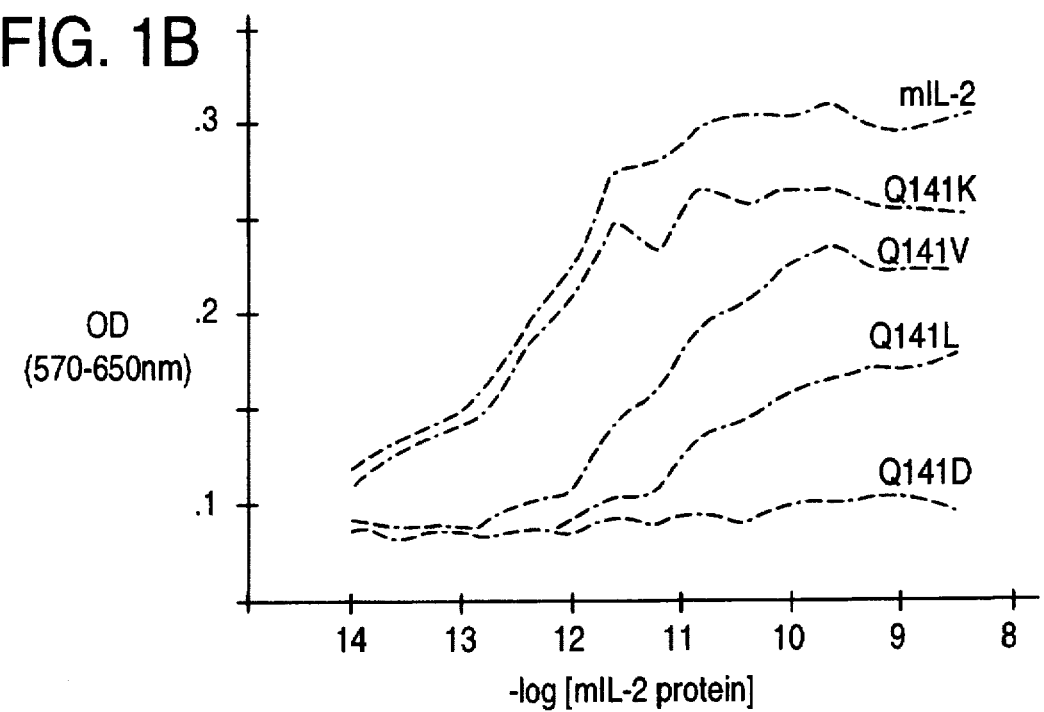
Figure 4A:
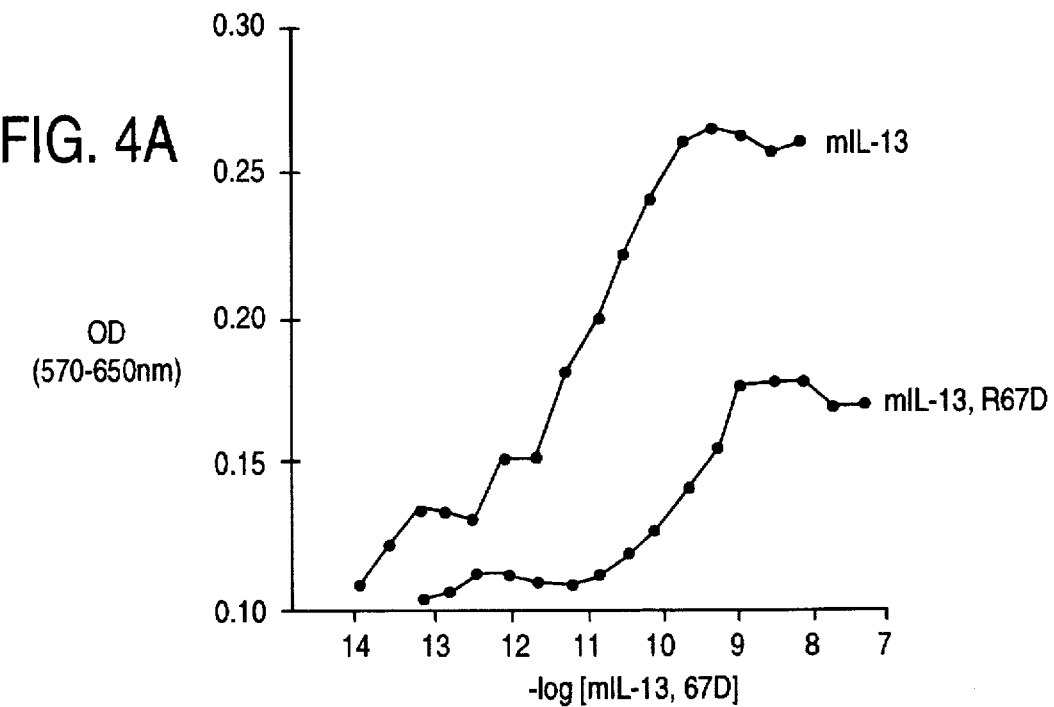
FIG. 4A–4B show partial agonist and antagonist activity of mouse IL-13 mutein R67D on B9 cells (see Brackenhoff, et al. (1994) *J. Biol. Chem.* 269:86–93).
Figure 4B:
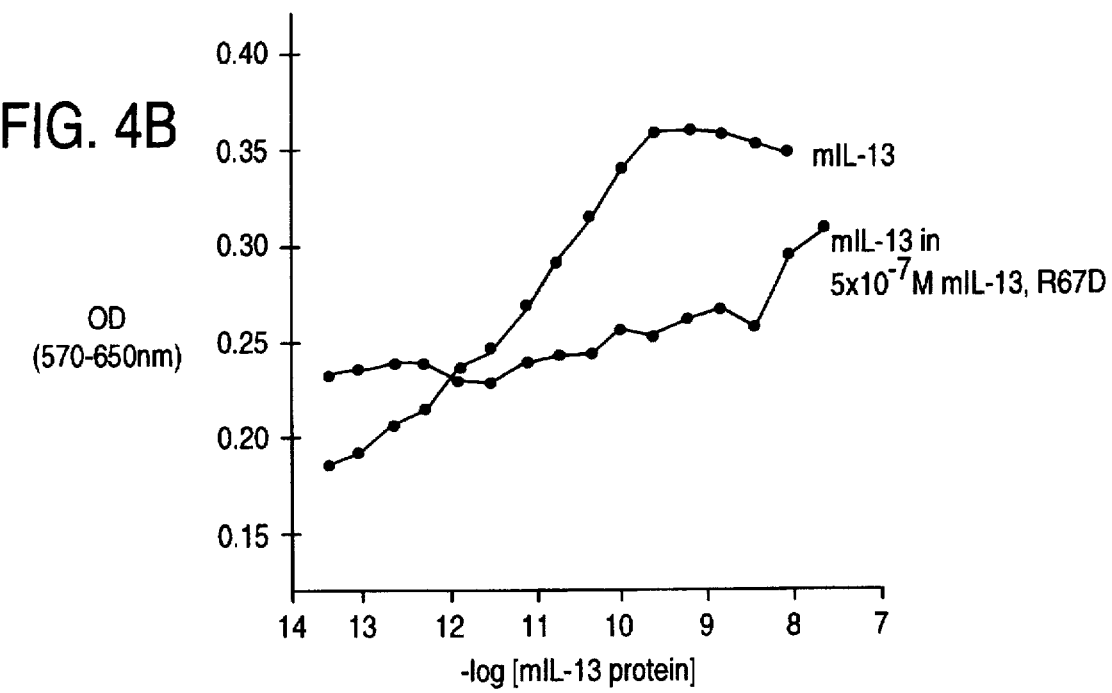

DETAILED DESCRIPTION OF THE
PREFERRED EMBODIMENTS

OUTLINE

I. General
II. Agonists; antagonists
III. Physical Variants
   A. fragments
   B. post-translational variants
      1. glycosylation
      2. others
   C. species variants
IV. Nucleic Acids
   A. mutated natural isolates; methods
   B. synthetic genes
   C. methods to isolate
V. Antibodies
   A. polyclonal
   B. monoclonal
   C. fragments, binding compositions
VI. Making Antagonists
   A. recombinant methods
   B. synthetic methods
   C. natural purification
VII. Uses A. diagnostic
B. therapeutic
VIII. Kits
A. nucleic acid reagents
B. protein reagents
C. antibody reagents

General

Extensive research has suggested that one cell communicates with another cell through discrete chemical molecules known as cytokines. Involvement of cytokines in a wide variety of diseases has been found, including cancer, allergy, infection, inflammation, wound healing, angiogenesis, differentiation, morphogenesis, and embryogenesis.

The present invention provides sequence variants of cytokines, e.g., muteins, which serve as antagonists of the cytokines. The natural ligands are capable of mediating various biochemical responses which should lead to biological or physiological responses in target cells, e.g., as described above.

Physically, relevant cytokines have been described, as shown in Table 1. The table provides the GenBank accession numbers of each cytokine, and references providing gene and/or cytokine amino acid sequence. Many receptor sequences are also available from GenBank. See also Howard, et al. (1993) in Paul (ed.) (1993) *Fundamental immunology* (3d ed.) Raven Press, N.Y.

TABLE 1

Cytokines and references.

| cytokine | GenBank # | Reference |
|---|---|---|
| mGM-CSF | X03221 | Gough, et al. (1984) Nature 309:763–767 |
| hGM-CSF | M6445 | Lee, et al. (1985) PNAS 82 4360–4364; Wong, et al. (1985) Cancer Cells 3:235–242 |
| mIL-2 | M16760–62 | see Arai, et al. (1990) Ann. Rev. Biochem. 59:783–836 |
| hIL-2 | J00264 | Fujita, et al. (1983) PNAS 80:7437–7441 |
| mIL-3 | K03233 | Fung, et al. (1984) Nature 307:233–237 |
| hIL-3 | M14743 M20137 M33135 | Yang, et al. (1986) Cell 47:3–10 |
| mIL-4 | M29854 | Howard, et al. (1984) Immunol. Revs. 78:185–210; Swain, et al. (1983) J. Expt'l Med. 158:822–835 |
| hIL-4 | M13982 | Yokota, et al. (1986) PNAS 83:5894–5898 |
| mIL-5 | X06270 | Kinashi, et al. (1986) Nature 324:70–73 |
| hIL-5 | X04688 | Kinashi, et al. (1986) Nature 324:70–73 |
| mIL-7 | X07962 | Lupton, et al. (1990) J. Immunol. 144:3592–3601 |
| hIL-7 | J04156 | Lupton, et al. (1990) J. Immunol. 144:3592–3601 |
| mIL-9 | X14045 | Van Snick, et al. (1989) J. Expt'l Med. 169:363–372 |
| hIL-9 | X17543 M30134 | Yang, et al. (1989) Blood 74:1880–1884; Renauld, et al. (1990) J. Immunol. 144:4235–4243 |
| IL-15 | U03099 | Grabstein, et al. (1994) Science 264:965–968 |

Corresponding bioassays are described, e.g., in Aggarwal and Gutterman (eds.) (1991) *Human Cytokines; Handbook for Basic and Clinical Research*, Blackwell, Oxford. These assays are useful in screening for partial agonist or antagonist activities.

Typical IL-2 bioassay: see Gillis, et al. (1978) *J. Immunol.* 120:2027–2031.

Typical IL-3 bioassay: growth of IL-3 responsive cells; see Lange, et al. (1987) *Blood* 70:192–199; Avanzi, et al. (1988) *Br. J. Haematol.* 69:359–366. This cytokine also exhibits growth and differentiation effects on neutrophils, macrophages, megakaryocytes, erythrocytes, eosinophils, basophils, and mast cells; stimulates the function of mature mast cells, basophils, eosinophils, and macrophages.

Typical IL-4 assays: see Spits, et al. (1987) *J. Immunol.* 139:1142–1147. This cytokine also exhibits effects on T cells, thymocytes, Natural Killer (NK) cells, Lymphocyte Activated Killer (LAK) cells, B cells, Burkitt's Lymphoma cells, B cell lymphomas, monocytes, hematopoietic precursor cells, eosinophils, neutrophils, and endothelial cells.

Typical IL-5 assays: see Kitamura, et al. (1989) *J. Cell. Physiol.* 140:323–334. This cytokine also exhibits effects on T cells, B cells, hematopoietic progenitor cells, and eosinophils.

Typical IL-7 assays: effects on IL-7 responsive cells, see Namen, et al. (1988) *Nature* 333:571–573; Sudo, et al. (1989) *J. Expt'l Med.* 170:333–338. This cytokine also exhibits effects on B cell progenitors and thymocytes.

Typical IL-9 assays: see Yang, et al. (1989) *Blood* 74:1880–1884; Renauld, et al. (1990) *J. Immunol.* 144:4235–4243.

Typical IL-13 assays: described, e.g., in Minty, et al. (1993) *Nature* 362:248–250; and McKenzie, et al. (1993) *Proc. Nat'l Acad. Sci. USA* 90:3735–3739; and see Zurawski and de Vries (1994) Immunol. Today 15:19–26.

Typical IL-15 assays: see Grabstein, et al. (1994) *Science* 264:965–968.

For the assays described herein, typically one finds a cell line whose growth is factor dependent and specific for a desired cytokine. Exemplary cell lines are: for mouse GM-CSF, NFS60. (see Holmes, et al. (1985) *Proc. Nat'l Acad. Sci. USA* 82:6687–6691); for human GM-CSF, use TF-1; for mouse IL-2, use HT2 cells; for human IL-2, use Kit225 cells or mouse Baf3 cells transformed with human IL-2R subunits α and β; for mouse IL-3, use NFS60; for human IL-3, use TF-1; for mouse IL-4, use HT2 cells; for human IL-4, use TF-1 cells; for mouse IL-5, use NFS60; for human IL-5, use TF-1; for human IL-7, use thymocyte cell lines; for human IL-9, use M07E cells, see Yang, et al. (1989) Blood 74:1880–1884; for both mouse and human IL-13, use TF-1 cells; for IL-15, use YT cells, see Yodoi, et al. (1985) *J. Immunol,* 134:1623–1630.

With a selected cell line, a dose-response curve of the appropriate cytokine is performed. This gives a plateau, or maximal stimulation at saturating or excess amounts of cytokine. Typically, the cytokine will show a useful dose-response in the range of $10^{-7}$ to $10^{-13}$ M cytokine. The half maximal response typically will fall in the range of $10^{-9}$ to $10^{-12}$ M.

A mutein candidate agonist is tested, preferably with a sequence substitution as described, by titrating a dose response curve of the cytokine in the absence or presence of the candidate mutein at a fixed concentration. Typically the candidate mutein concentration is fixed, preferably within the range of equimolar to the half-maximum of the target cytokine, or at a 10-, 100-, or 1000- fold excess of candidate mutein over that half-maximum amount. Typically, the dose response curve of the cytokine will shift. The shift will normally be at least one log unit, often two to four log units.

To test partial agonist activity of the candidate mutein, a dose-response curve of the mutein is performed. Typically, the maximal stimulatory activity of the mutein will be near that of the natural cytokine, but partial agonists will show a suboptimal stimulation at saturation, e.g., the maximal activity will plateau at a lesser amount. This amount will often be less than about 90%, preferably less than about 75%, more preferably less than about 50%, and in most preferred embodiments, even less than about 25%. Agonists with an even lesser maximum will still be useful, and often provide the most promising candidates for establishing chemical antagonist properties.

Specific analyses for IL-2 and IL-13 are shown in the figures. Similar analysis can be performed with the GM-CSF, IL-3, and IL-5 series of muteins. These three cytokines share similarities in their receptor behavior due, in part, to sharing of receptor structures. Similarities also exist for IL-7, IL-9, and IL-15, due also, apparently, to shared receptor structures. Muteins are made typically by site specific mutagenesis of natural cytokine at defined positions. The sequences of the cytokines are referred to in Table 1, GenBank, and the references cited therein. Initially, single and low multiplicity mutagenesis will be constructed, with more complex combinations also available. The tertiary structural features of the cytokines have been described, e.g., in Bazan (1991) *Cell* 66:9–10; Bazan (1990) *Immunology Today* 11:350–354; Bazan (1992) *Science* 257:410–413; Rozwarski, et al. (1994) *Structure* 2:159-173; and Sprang and Bazan (1993) *Current Opinion in Structural Biology* 3:815–827. These references define common structural features of the cytokines, e.g., the helices A, B, C, and D therein, including sequence alignments and corresponding positions. See also Zurawski, et al. (1993) *EMBO J.* 12:2663–2670. Helix C of human IL-13 runs from residue 57 (S) to 69 (F), and in mouse P600 from residue 60 (N) to 72 (L). The specific positions of critical substitutions typically are conserved across different cytokines in various patterns, and because the helical turn involves 3.5 residues per turn, 3 or 4 residues and 7 residues in either direction will be positioned adjacent on the surface of a cytokine.

II. Agonists; antagonists

The process of inhibition or prevention of agonist-induced responses is termed antagonism, and chemical entities with such properties are antagonists. See, e.g., Kenakin (1987).

Pharmacological Analysis of Drug-Recepter Interaction Raven Press, N.Y.

Various classes of antagonists include chemical or neutralization antagonists, competitive antagonists, and noncompetitive antagonists. The chemical or neutralization antagonists interact with the agonist and prevent activation of the receptor and subsequent response, e.g., antibody antagonists which bind to the agonist and block signaling thereby.

The competitive antagonists are molecules which bind to the same recognition site on the receptor and block agonist binding. Noncompetitive antagonists bind to a site on the receptor distinct from the agonist binding site, and block signal transduction.

Measurement of antagonist activity and analysis of these results can be performed by Schild analysis. See Arunlakshana and Schild (1959) *Br. J. of Pharmacol.* 14:14–58; and Chapter 9 of Kenakin (1987) *Pharmacological Analysis of Drug-Receptor Interaction* Raven Press, N.Y. See also Black (1989) *Science* 245:486–493. Schild analysis with a defined antagonist provides a number of means to evaluate quantity and quality of both agonist and receptor preparations. For example, analysis of a preparation of agonist allows better quality control indications than ELISA or mere bioassay quantitation methods. It provides means to distinguish between a denatured agonist, which is more likely to test positive in ELISA assays, and a biologically active agonist.

The described muteins are typically proteinaceous, though a full length is not necessary. Fragments can be useful where they include positions which have been mutated as provided herein.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids. Virtually full length molecules with few substitutions will be preferred in most circumstances.

Substantially pure typically means that the mutein is free from other contaminating proteins, nucleic acids, and other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS or CHAPS, or a low enough concentration as to avoid significant disruption of structural or physiological properties of the ligand.

III. Physical Variants

This invention also encompasses proteins or peptides having sequence variations at positions corresponding to the specified residues, but with substantial amino acid sequence identity at other segments. The variants include species variants and particularly molecules with the same primary sequence but variations beyond primary amino acid sequence, e.g., glycosylation or other modifications.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Wraps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis;. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Substitutions at designated positions can often be made with homologous residues to retain similar activities, e.g., agonist or antagonist functions. Identity measures will be at least about 85%, usually at least about 95%, preferably at least about 97%, and more preferably at least 98% or more, especially about the particular residue positions identified as appropriate for sequence changes. Regions of particular importance are within about 5 amino acids surrounding the defined positions, more particularly within about 8 amino acids, and preferably within about 11 amino acids adjacent the positions where changes are indicated.

The isolated cytokine DNA can be readily modified by nucleotide substitutions, nucleotide deletions, nucleotide insertions, and inversions of nucleotide stretches. These modifications result in novel DNA sequences which encode these proteins having many similar physiological, immunogenic, antigenic, or other functional activity. Enhanced expression may involve gene amplification, increased transcription, increased translation, and other mechanisms.

Cytokine mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Meth. Enzymol,* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Terra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

"Derivatives" of these cytokines include amino acid sequence mutants at other positions remote from those specified, glycosylation variants, and covalent or aggregate conjugates with other chemical moieties. Covalent derivatives can be prepared by linkage of functibnalities to groups which are found in amino acid side chains or at the N- or C-termini, by standard means. See, e.g., Lundblad and Noyes (1988) *Chemical Reagents for Protein Modification,* vols. 1–2, CRC Press, Inc., Boca Raton, Fla.; Hugli (ed.) (1989) *Techniaues in Protein Chemistry,* Academic Press, San Diego, Calif.; and Wong (1991). *Chemistry of Protein Conjugation and Cross Linking,* CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between these cytokine muteins and other homologous or heterologous proteins are also provided. Many growth factors and cytokines are homodimeric entities, and a repeat construct may have various advantages, including lessened susceptibility to proteolytic cleavage. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology,* Greene and Wiley, N.Y. Techniques for synthesis of potypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach,* IRL Press, Oxford; and Grant (1992) *Synthetic Peptides: A User's Guide,* W. H. Freeman, N.Y.

This invention also contemplates the use of derivatives of these cytokine muteins other than variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of receptors or other binding ligands. A cytokine mutein can be immobilized by covalent bonding to a solid support such as cyanogen bromide-activated SEPHAROSE, by methods which are well known in the art, or adsorbed onto polyotefin surfaces, with or without glutaraldehyde cross-linking, for use in the assay or purification of anti-cytokine antibodies or its receptor. The cytokine muteins can also be labeled with a detectable group, for use in diagnostic assays. Purification of cytokine muteins may be effected by immobilized antibodies or receptor.

The present invention contemplates corresponding muteins the isolation of additional closely related species variants, e.g., rodents, lagomorphs, carnivores, artiodactyla, perissodactyla, and primates.

The invention also provides means to isolate a group of related muteins displaying both distinctness and similarities in structure, expression, and function. Elucidation of many of the physiological effects of the muteins will be greatly accelerated by the isolation and characterization of distinct species variants.

The isolated genes encoding muteins will allow transformation of cells lacking expression of a corresponding cytokine, e.g., either species types or cells which exhibit negative background activity.

Dissection of critical structural elements which effect the various receptor mediated functions provided by cytokine binding is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem*, 263:15985–15992; and Lechleiter, et al. (1990) *EMBO J.* 9:4381–4390.

IV. Nucleic Acids

The described peptide sequences are readily made by expressing a DNA clone encoding the mutein, e.g., modified from a natural source. A number of different approaches should be available to successfully produce a suitable nucleic acid clone.

The purified protein or defined peptides are useful as described above. Synthetic peptides or purified protein can be presented to an immune system to generate monoclonal or polyclonal antibodies which recognize specifically the muteins. See, e.g., Coligan (1991) *Current Protocols in Immunology* Wiley/Greene; and Harlow and Lane (1989) *Antibodies: A Laboratory Manual*, Cold Spring Harbor Press.

This invention contemplates use of isolated DNA or fragments to encode a biologically active corresponding mutein. In addition, this invention covers isolated or recombinant DNA which encodes a biologically active antagonist or partial agonist protein or polypeptide.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

Recombinant clones derived from genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach*, IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence encoding a mutein.

V. Antibodies

Antibodies can be raised to portions of cytokines which bind to the muteins described herein, including species or allelic variants, and fragments thereof. Additionally, antibodies can be raised to cytokine muteins in either their active forms or in their inactive forms. Anti-idiotypic antibodies are also contemplated.

Antibodies, including binding fragments and single chain versions, against predetermined fragments of the ligands can be raised by immunization of animals with conjugates of fragments with immunogenic proteins. Monoclonal antibodies are prepared from cells secreting the desired antibody. These antibodies can be screened for binding to fragments containing sequences including the specified modifications. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies of this invention can also be useful in diagnostic applications. See e.g., Chan (ed.) (1987) *Immunology: A Practical Guide*, Academic Press, Orlando, Fla.; Price and Newman (eds.) (1991) *Principles and Practice of Immunoassay*, Stockton Press, N.Y.; and Ngo (ed.) (1988) *Nonisotopic Immunoassay*, Plenum Press, N.Y.

Mutein fragments may be joined to other materials, particularly polypeptides, as fused or covalently joined polypeptides to be used as immunogens. A mutein or its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, N.Y.; and Harlow and Lane (1988) *Antibodies: A Laboratory Manual*, CSH Press, New York, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each mutein will also be useful to raise anti-idiotypic antibodies. These will be useful in detecting or diagnosing various immunological conditions related to expression of the respective antigens.

VI. Making Agonists and Antagonists

DNA which encodes the cytokines or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 1.2:161–170; Gubler and Hoffman (1983) *Gene* 25:26.3–269; and Glover (ed.) (1984) *DNA Cloning: A Practical Approach*, IRL Press, Oxford. Suitable sequences can be obtained from GenBank.

This DNA can be mutated for expression in a wide variety of host cells for the synthesis of a full-length mutein or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; Rodriguez, et al. (1988)(eds.) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current protocols in Molecular Biology*, Greene and Wiley, New York.

Representative examples of suitable expression vectors include pCDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express a mutein or polypeptide in a system which provides a specific or defined glycosylation pattern. See, e.g., Luckow and Summers (1988) *Bio/Technology* 6:47–55; and Kaufman (1990) *Meth. Enzymol*, 185:487–511.

The appropriate mutein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Once a particular mutein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; and Villafranca (ed.) (1991) *Techniques in Protein Chemistry II*, Academic Press, San Diego, Calif.

VII. Uses

The present invention provides reagents which will find use in diagnostic applications as described elsewhere herein, e.g., in the general description for developmental abnormalities, or below in the description of kits for diagnosis.

The cytokine muteins, fragments thereof, and antibodies thereto, should be useful in the evaluation or quality control of recombinant production of various cytokines. They may also be useful in vitro or in vivo screening or treatment of conditions associated with abnormal physiology or development, including abnormal proliferation, e.g., cancerous conditions, or degenerative conditions. In particular, modulation of cytokine activities should be useful in situations where the cytokine functions have been implicated, e.g., immunological responses, inflammation, autoimmunity, abnormal proliferation, regeneration, degeneration, and atrophy of responsive cell types. For example, a disease or disorder associated with abnormal expression or abnormal signaling by a cytokine should be a likely target for treatment using an antagonist or agonist.

Other abnormal or inappropriate physiological or developmental conditions are known in each of the cell types shown to be responsive to the specified cytokines. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. For example, neural and brain abnormalities exist in, e.g., cerebrovascular disease, CNS neoplasms, demyelinating diseases, and muscular dystrophies. Liver disorders, kidney disorders, cardiopulmonary disorders, and other problems often cause medical symptoms. These problems may be susceptible to prevention or treatment using compositions provided herein.

For example, the IL-2 muteins would be useful in mediating immune suppression or IL-2 dependent proliferation, e.g., in certain lymphomas. IL-13 muteins would be useful in modulating IgE mediated responses and other IL-13 mediated responses. Similar uses will be found with the GM-CSF, IL-3, IL-5, IL-7, IL-9, and IL-15 muteins.

Recombinant cytokine muteins or, in some instances, antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration. See, e.g., Langer (1990) *Science* 49:1527–1533.

These cytokine muteins may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications*, Dekker, New York; Lieberman, et al. (eds.) (1990) *Pharmaceutical Dosage Forms: Tablets*, Dekker, New York; and Lieberman, et al. (eds.) (1990) *Pharmaceutical Dosage Forms: Disoerse Systems*, Dekker, New York. The therapy of this invention may be combined with or used in association with other agents.

The muteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate.

For example, antagonists can normally be found once the ligand has been structurally defined. Testing of potential ligand analogs is now possible. In particular, new agonists and antagonists will be discovered by using screening techniques described herein. Of particular importance are compounds found to have a combined binding affinity for multiple cytokine receptors, e.g., compounds which can serve as antagonists for a plurality of cytokines.

One method of drug screening utilizes eukaryotic or prokaryotic host cells which are stably transformed with recombinant DNA molecules expressing the cytokine receptor. Cells may be isolated which express a receptor in isolation from any others. Such cells, either in viable or fixed form, can be used for standard ligand/receptor binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Rational drug design may also be based upon structural studies of the molecular shapes of the agonists or antagonists and other effectors or analogs. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

VIII. Kits

This invention also contemplates use of these muteins, proteins, fragments thereof, peptides, and their fusion products in a variety of diagnostic kits and methods for diagnosing the receptor interactions of a cytokine. Typically the kit will have a compartment containing either a defined mutein peptide or a reagent which recognizes one, e.g., receptor fragments or antibodies.

A kit for determining the binding affinity of a test compound to a receptor would typically comprise a test compound; a labeled compound, for example a receptor or antibody having known binding affinity for the cytokine or its mutein; a source of mutein; and a means for separating bound from free labeled compound, such as a solid phase for immobilizing the mutein. Once compounds are screened, those having suitable binding affinity to the receptor can be evaluated in suitable biological assays, as are well known in the art, to determine whether they act as agonists or antagonists to the receptor.

Antibodies, including antigen binding fragments, specific for muteins or unique fragments are useful in diagnostic applications to detect the presence of the muteins. In certain circumstances, it will be useful to quantitate amounts of muteins in a sample. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol*, 70:1–525; Harlow and Lane (1980) *Antibodies: A Laboratory Manual*, CSH Press, N.Y.; and Coligan, et al. (eds.) (1993) *Current Protocols in Immunology*, Greene and Wiley, N.Y.

Anti-idiotypic antibodies may have similar use to diagnose presence of antibodies against a mutein, as such may be diagnostic of various abnormal states.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled mutein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the test compound, mutein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940, 475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The mutein can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, New York. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

All references cited herein are incorporated herein by reference to the same extent as if each individual publication or patent application was specifically and individually indicated to be incorporated by reference.

The broad scope of this invention is best understood with reference to the following examples, which are not intended to limit the invention to specific embodiments.

EXAMPLES

General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual* (2d ed.), vols 1–3, CSH Press, N.Y.; Ausubel, et al., *Biology*, Greene Publishing Associates, Brooklyn, N.Y.; or Ausubel, et al.

(1987 and Supplements) *Current Protocols in Molecular Biology*, Greene and Wiley, New York; Innis, et al. (eds.) (1990) *PCR Protocols: A Guide to Methods and Applications*, Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmadia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) Genetic Engineering, *Principle and Methods* 12:87–98, Plenum Press, N.Y.; and Crowe, et al. (1992) *OlAexpress: The High Level Expression & Protein Purification System* QUIAGEN, Inc., Chatsworth, Calif. Cell culture techniques are described in Doyle, et al. (eds.) (1994) *Cell and Tissue Culture: Laboratory procedures*, John Wiley and Sons, New York.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Substitution Analysis of cytokines.

Methods for expression of a mutein cytokine in *E. coli* are described in Zurawski, et al. (1986) *J. Immunol.* 137:3354–3360; and Zurawski and Zurawski, et al. (1988) *EMBO J.* 7:1061–1069. Cassette substitution mutagenesis is described in Zurawski and Zurawski (1989) *EMBO J.* 8:2583–2590. Preparation and biological assay of crude extracts of mutant IL-2 proteins in the presence and absence of IL-2 antagonist is described in Zurawski and Zurawski (1988) *EMBO J.* 7:1061–1069; and Zurawski, et al. (1992) *EMBO J*, 11:3905–3910. The IL-2 muteins are prototypes for similar constructs and assays for other cytokines, both for cytokines which share these receptor subunits, and other cytokines exhibiting specific structural and/or functional similarity. See, e.g., Zurawski, et al. (1993) *EMBO J.* 12:2663–2670; and Zurawski, et al. (1993) *EMBO J.* 12:5113–5119. Similar analysis or screening of defined constructs for other cytokines, e.g., IL-13 muteins, are made by similar methods.

Receptor Binding Analysis

Receptor binding analyses for IL-2 were performed on L cells expressing mIL-2Rα the A22 cell line, as described in Zurawski and Zurawski (1992) *EMBO J.* 11:3905–3910. Assays used included a heterologous displacement format with labeled ligand ($[^{125}I]$hIL-2, IM247 from Amersham; or $[^{32}P]$mIL-2.P2, see Imler and Zurawski (1992) *J. Biol. Chem*, 267:13185–13190) at $10^{-9}$M and various concentrations of purified mIL-2 or mutant mIL-2 proteins. mIL-2 proteins were purified as described by Zurawski and Zurawski (1992) *EMBO J.* 11:3905–3910. Data for mIL-2 and various representative mIL-2 muteins were analyzed using the Ligand computer program, see Munson and Rodbard (1980) *Anal. Biochem.* 107:220–239. Receptor binding analyses were also performed on L cells expressing mIL-2Rαβ, derived by cotransfection by expression plasmids for the two receptor subunits, except the labeled ligand was at $10^{-11}$ M.

Similar analysis is applied to other cytokines, as described. Corresponding receptor subunits for transfection into cells with no binding capacity are available from published sequences.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A mutein of:
1) human IL-13, said mutein exhibiting both:
  a) antagonist activity; and
  b) a substitution in sequence between 57 (set) and 69 (phe); or
2) a mouse P600, said mutein exhibiting both:
  a) antagonist activity; and
  b) a substitution in sequence between 60 (asn) and 72 (leu).

2. A mutein of claim 1, wherein said mutein:
a) exhibits less than 80% maximal agonist activity; and/or
b) at a 100-fold excess antagonizes said activity by at least 50%.

3. The mutein of claim 2, wherein said substitution to:
1) human IL-13 corresponds to position 64 (arg); or
2) mouse P600 corresponds to position 67 (arg).

4. The mutein of claim 1, wherein said substitution to:
1) human IL-13 corresponds to position 64 (arg); or
2) mouse P600 corresponds to position 67 (arg).

5. The mutein of claim 4, wherein said substitution to:
1) human IL-13 corresponding to position 64 (arg) is an acidic amino acid; or
2) mouse P600 corresponding to position 67 (arg) is an acidic amino acid.

6. The mutein of claim 5, comprising a sequence selected from:

a) [kLIEELVNIT QNQKAPLCNG SMVWSINLTA GMYCAALESL INVSGCSAIE KTQdMLSGFC (see SEQ ID NO: 5)] lys Leu Ile Glu Glu Leu Val Asn Ile Thr Gln Asn Gln Lys Ala Pro Leu Cys Asn Gly Ser Met Val Trp Set Ile Asn Leu Thr Ala Gly Met Tyr Cys Ala Ala Leu Glu Ser Leu Ile Asn Val Ser Gly Cys Ser Ala Ile Glu Lys Thr Gln asp Met Leu Ser Gly Phe Cys (Residues 11–70 of SEQ ID NO: 15);

b) [PHKVSAGQFS SLHVRDTKIE VAQFVKDLLL (see SEQ ID NO: 4)] Pro His Lys Val Ser Ala Gly Gln Phe Ser Ser Leu His Val Arg Asp Thr Lys Ile Glu Val Ala Gln Phe Val Lys Asp Leu Leu Leu (Residues 71–100 of SEQ ID NO: 14); or c) [LAAGGFCVAL DSLTNISNCN AIYRTQdILH GLCNRKAPTT VSSLPDTKIE VAHFTTKLLS (see SEQ ID NO: 6)]Leu Ala Ala Gly Gly Phe Cys Val Ala Leu Asp Ser Leu Thr Asn Ile Ser Asn Cys Asn Ala Ile Tyr Arg Thr Gln asp Ile Leu His Gly Leu Cys Asn Arg Lys Ala Pro Thr Thr Val Ser Ser Leu Pro Asp Thr Lys Ile Gly Val Ala His Phe Ile Thr Lys Leu Leu Ser (Residues 41–100 of SEQ ID NO:16).

7. A protein comprising a sequence:

a) [GPVPPSTALR kLIEELVNIT QNQKAPLCNG SMVWSTNLTA GMYCAALESL INVSGCSAIE KTQdMLSGFC PHKVSAGQFS SLHVRDTKIE VAQFVKDLLL HLKKLFREGR FN] Gly Pro Val Pro Pro Ser Thr Ala Leu Arg lys Leu Ile Glu Glu Leu Val Asn Ile Thr Gln Asn Gln Lys Ala Pro Leu Cys Asn Gly Ser Met Val Trp Ser Ile Asn Leu Thr Ala Gly Met Tyr Cys Ala Ala Leu Glu Ser Leu Ile Asn Val Ser Gly Cys Ser Ala Ile Glu Lys Thr Gln asp Met Leu Ser Gly Phe Cys Pro His Lys Val Ser Ala Gly Gln Phe Ser Ser Leu His Val Ala Asn Thr Lys Ile Glu Val Ala Gln Phe Val Lys Asp Leu Leu His Leu Lys Lys Leu Phe Arg Glu Gly Arg Phe Asn (see SEQ ID NO: 14);

b) [GPVPPSTALR kLIEELVNIT QNQKAPLCNG SMVWSINLTA GMYCAALFSL TNVSGCSATE KTQdMLSGFC PHKVSAG-FS SLHVRDTKTE VAQFVKDLLL HLKKLFREGR FN] Gly Pro Val Pro Pro Ser Thr Ala Leu Arg lys Leu Ile Glu Glu Leu Val Asn Ile Thr Gln Asn Gln Lys Ala Pro Leu Cys Asn Gly Ser Met Val Trp Ser Ile Asn Leu Thr Ala Gly Met Tyr Cys Ala Ala Leu Glu Ser Leu Ile Asn Val Ser Gly Cys Ser Ala Ile Glu Lys Thr Gln asp Met Leu Ser Gly Phe Cys Pro His Lys Val Ser Ala Gly Phe Ser Ser Leu His Val Arg Asp Thr Lys Ile Glu Val Ala Gln Phe Val Lys Asp Leu Leu His Leu Lys Lys Leu Phe Arg Glu Gly Arg Phe Asn (see SEQ ID NO: 15); or c) [GPVPRSVSLP LTLKELIEEL SNITQDETPL CNGSMVWSVD LAAGGFCVAL DSLTNTSNCN AIYRTQdILH GLCNRKAPTT VSSLPDTKIE VAHFITKLLS YTKQLFRHGP F] Gly Pro Val Pro Arg Ser Val Ser Leu Pro Leu Thr Leu Lys Glu Leu Ile Glu Glu Leu Ser Asn Ile Thr Gln Asp Glu Thr Pro Leu Cys Asn Gly Ser Met Val Trp Ser Val Asp Leu Ala Ala Gly Gly Phe Cys Val Ala Leu Asp Ser Leu Thr Asn Ile Ser Asn Cys Asn Ala Ile Tyr Arg Thr Gln asp Ile Leu His Gly Leu Cys Asn Arg Lys Ala Pro Thr Thr Val Ser Ser Leu Pro Asp Thr Lys Ile Glu Val Ala His Phe Ile Thr Lys Leu Leu Ser Tyr Thr Lys Gln Leu Phe Arg His Gly Pro Phe (see SEQ ID NO: 16).

8. A pharmaceutical composition comprising a mutein of claim 1, and a pharmaceutically acceptable carrier.

9. The mutein of claim 1, wherein said helix C runs:
1) in human IL-13 from 57 (ser) to 69 (phe); or
2) in mouse P600 from 60 (ash) to 72 (leu).

10. The mutein of claim 5, wherein:
a) said acidic amino acid is aspartic acid; or
b) said acidic amino acid is aspartic acid and said mutein is:
i) in a sterile composition;
ii) at least about 40% pure; or
iii) detectably labeled.

11. A mutein of:
1) human IL-13 having a sequence selected from the group consisting of:

i) [GPVPPSTALR eLIEELVNIT QNQKAPLCNG SMVWSINLTA GMYCAALESL INVSGCSAIE KTQrMLSGFC PHKVSAGQFS SLHVRDTKIE VAQFVKDLLL HLKKLFREGR FN] Gly Pro Val Pro Pro Ser Thr Ala Leu Arg glu Leu Ile Glu Glu Leu Val Asn Ile Thr Gln Asn Gln Lys Ala Pro Leu Cys Asn Gly Ser Met Val Trp Ser Ile Asn Leu Thr Ala Gly Met Tyr Cys Ala Ala Leu Glu Ser Leu Ile Asn Val Ser Gly Cys Ser Ala Ile Glu Lys Thr Gln arg Met Leu Ser Gly Phe Cys Pro His Lys Val Ser Ala Gly Gln Phe Ser Ser Leu His Val Arg Asp Thr Lys Ile Glu Val Ala Gln Phe Val Lys Asp Leu Leu His Leu Lys Lys Leu Phe Arg Glu Gly Arg Phe Asn (see SEQ ID NO: 4); and ii) [GPVPPSTALR eLIEELVNIT QNQKAPLCNG SMVWSINLTA GMYCAALESL INVSGCSAIE KTQrMLSGFC PHKVSAG-FS SLHVRDTKIE VAQFVKDLLL HLKKLFREGR FN] Gly Pro Val Pro Pro Ser Thr Ala Leu Arg glu Leu Ile Glu Glu Leu Val Asn Ile Thr Gln Asn Gln Lys Ala Pro Leu Cys Asn Gly Ser Met Val Trp Ser Ile Asn Leu Thr Ala Gly Met Tyr Cys Ala Ala Leu Glu Ser Leu Ile Asn Val Ser Gly Cys Ser Ala Ile Glu Lys Thr Gln arg Met Leu Ser Gly Phe Cys Pro His Lys Val Ser Ala Gly Phe Ser Ser Leu His Val Arg Asp Thr Lys Ile Glu Val Ala Gly Phe Val Lys

```
Asp Leu Leu Leu His Leu Lys Lys Leu Phe Arg Glu Gly
Arg Phe Asn (see SEQ ID NO: 5);
``` said mutein exhibiting both:
  a) antagonist activity; and
  b) a substitution in sequence between 57 (ser) and 69 (phe); or
2) a mouse P600 having a sequence of

```
[GPVPRSVSLP LTLKELIEEL
SNITQDETPL CNGSMVWSVD LAAGGFCVAL DSLTNISNCN
AIYRTQrILH GLCNRKAPTT VSSLPDTKIE VAHFITKLLS
YTKQLFRHGP F] Gly Pro Val
Pro Arg Ser Val Ser Leu Pro Leu Thr Leu Lys Glu Leu Ile
Glu Glu Leu Ser Asn Ile Thr Gln Asp Glu Thr Pro Leu Cys
Asn Gly Ser Met Val Trp Ser Val Asp Leu Ala Ala Gly Gly
Phe Cys Val Ala Leu Asp Ser Leu Thr Asn Ile Ser Asn Cys
```

```
Asn Ala Ile Tyr Arg Thr Gln arg Ile Leu His Gly Leu Cys
Asn Arg Lys Ala Pro Thr Thr Val Ser Ser Leu Pro Asp Thr
Lys Ile Glu Val Ala His Phe Ile Thr Lys Leu Leu Ser Tyr
Thr Lys Gln Leu Phe Arg His Gly Pro Phe (see SEQ ID NO: 6).
``` said mutein exhibiting both:
  a) antagonist activity; and
  b) a substitution in sequence between 60 (asn) and 72 (leu).

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 133 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala  Pro  Thr  Ser  Ser  Ser  Thr  Lys  Lys  Thr  Gln  Leu  Gln  Leu  Glu  His
 1                 5                      10                      15

Leu  Leu  Leu  Asp  Leu  Gln  Met  Ile  Leu  Asn  Gly  Ile  Asn  Asn  Tyr  Lys
               20                      25                      30

Asn  Pro  Lys  Leu  Thr  Arg  Met  Leu  Thr  Phe  Lys  Phe  Tyr  Met  Pro  Lys
          35                      40                      45
```

```
Lys Ala Thr Glu Leu Lys His Leu Gln Cys Leu Glu Glu Leu Lys
    50              55              60

Pro Leu Glu Glu Val Leu Asn Leu Ala Gln Ser Lys Asn Phe His Leu
65              70              75              80

Arg Pro Arg Asp Leu Ile Ser Asn Ile Asn Val Ile Val Leu Glu Leu
            85              90              95

Lys Gly Ser Glu Thr Thr Phe Met Cys Glu Tyr Ala Asp Glu Thr Ala
            100             105             110

Thr Ile Val Glu Phe Leu Asn Arg Trp Ile Thr Phe Cys Gln Ser Ile
        115             120             125

Ile Ser Thr Leu Thr
        130
```

( 2 ) INFORMATION FOR SEQ ID NO:2:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
            35              40              45

Lys Ala Thr Glu Leu Lys His Leu Gln Cys Leu Glu Glu Glu Leu Lys
    50              55              60

Pro Leu Glu Glu Val Leu Asn Leu Ala Gln Ser Lys Asn Phe His Leu
65              70              75              80

Arg Pro Arg Asp Leu Ile Ser Asn Ile Asn Val Ile Val Leu Glu Leu
            85              90              95

Lys Gly Ser Glu Thr Thr Phe Met Cys Glu Thr Ala Asp Glu Thr Ala
            100             105             110

Thr Ile Val Glu Phe Leu Asn Arg Trp Ile Thr Phe Cys Gln Ser Ile
        115             120             125

Ile Ser Thr Leu Thr
        130
```

( 2 ) INFORMATION FOR SEQ ID NO:3:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
            35              40              45
```

```
    Lys   Ala   Thr   Glu   Leu   Lys   His   Leu   Gln   Cys   Leu   Glu   Glu   Leu   Lys
          50                            55                            60

Pro   Leu   Glu   Glu   Val   Leu   Asn   Leu   Ala   Gln   Ser   Lys   Asn   Phe   His   Leu
    65                            70                            75                            80

Arg   Pro   Arg   Asp   Leu   Ile   Ser   Asn   Ile   Asn   Val   Ile   Val   Leu   Glu   Leu
                            85                            90                            95

Lys   Gly   Ser   Glu   Thr   Thr   Phe   Met   Cys   Glu   Thr   Ala   Asp   Glu   Thr   Ala
                      100                           105                           110

Thr   Ile   Val   Glu   Phe   Leu   Asn   Arg   Trp   Ile   Thr   Phe   Ser   Gln   Ser   Ile
                      115                           120                           125

Ile   Ser   Thr   Leu   Thr
                      130
```

( 2 ) INFORMATION FOR SEQ ID NO:4:

( i ) SEQUENCE CHARACTERISTICS:
        ( A ) LENGTH: 112 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
    Gly   Pro   Val   Pro   Pro   Ser   Thr   Ala   Leu   Arg   Glu   Leu   Ile   Glu   Glu   Leu
    1                       5                             10                            15

Val   Asn   Ile   Thr   Gln   Asn   Gln   Lys   Ala   Pro   Leu   Cys   Asn   Gly   Ser   Met
                      20                            25                            30

Val   Trp   Ser   Ile   Asn   Leu   Thr   Ala   Gly   Met   Tyr   Cys   Ala   Ala   Leu   Glu
                      35                            40                            45

Ser   Leu   Ile   Asn   Val   Ser   Gly   Cys   Ser   Ala   Ile   Glu   Lys   Thr   Gln   Arg
                50                            55                            60

Met   Leu   Ser   Gly   Phe   Cys   Pro   His   Lys   Val   Ser   Ala   Gly   Gln   Phe   Ser
    65                            70                            75                            80

Ser   Leu   His   Val   Arg   Asp   Thr   Lys   Ile   Glu   Val   Ala   Gln   Phe   Val   Lys
                            85                            90                            95

Asp   Leu   Leu   Leu   His   Leu   Lys   Lys   Leu   Phe   Arg   Glu   Gly   Arg   Phe   Asn
                      100                           105                           110
```

( 2 ) INFORMATION FOR SEQ ID NO:5:

( i ) SEQUENCE CHARACTERISTICS:
        ( A ) LENGTH: 111 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
    Gly   Pro   Val   Pro   Pro   Ser   Thr   Ala   Leu   Arg   Glu   Leu   Ile   Glu   Glu   Leu
    1                       5                             10                            15

Val   Asn   Ile   Thr   Gln   Asn   Gln   Lys   Ala   Pro   Leu   Cys   Asn   Gly   Ser   Met
                      20                            25                            30

Val   Trp   Ser   Ile   Asn   Leu   Thr   Ala   Gly   Met   Tyr   Cys   Ala   Ala   Leu   Glu
                      35                            40                            45

Ser   Leu   Ile   Asn   Val   Ser   Gly   Cys   Ser   Ala   Ile   Glu   Lys   Thr   Gln   Arg
                50                            55                            60

Met   Leu   Ser   Gly   Phe   Cys   Pro   His   Lys   Val   Ser   Ala   Gly   Phe   Ser   Ser
    65                            70                            75                            80
```

```
        Leu  His  Val  Arg  Asp  Thr  Lys  Ile  Glu  Val  Ala  Gln  Phe  Val  Lys  Asp
                            85                  90                       95

Leu  Leu  Leu  His  Leu  Lys  Lys  Leu  Phe  Arg  Glu  Gly  Arg  Phe  Asn
                            100                      105                      110
```

( 2 ) INFORMATION FOR SEQ ID NO:6:

( i ) SEQUENCE CHARACTERISTICS:
        ( A ) LENGTH: 111 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
        Gly  Pro  Val  Pro  Arg  Ser  Val  Ser  Leu  Pro  Leu  Thr  Leu  Lys  Glu  Leu
        1                   5                        10                       15

Ile  Glu  Glu  Leu  Ser  Asn  Ile  Thr  Gln  Asp  Glu  Thr  Pro  Leu  Cys  Asn
                            20                       25                       30

Gly  Ser  Met  Val  Trp  Ser  Val  Asp  Leu  Ala  Ala  Gly  Gly  Phe  Cys  Val
                       35                       40                       45

Ala  Leu  Asp  Ser  Leu  Thr  Asn  Ile  Ser  Asn  Cys  Asn  Ala  Ile  Tyr  Arg
                  50                       55                  60

Thr  Gln  Arg  Ile  Leu  His  Gly  Leu  Cys  Asn  Arg  Lys  Ala  Pro  Thr  Thr
        65                            70                  75                       80

Val  Ser  Ser  Leu  Pro  Asp  Thr  Lys  Ile  Glu  Val  Ala  His  Phe  Ile  Thr
                            85                       90                       95

Lys  Leu  Leu  Ser  Tyr  Thr  Lys  Gln  Leu  Phe  Arg  His  Gly  Pro  Phe
                            100                      105                      110
```

( 2 ) INFORMATION FOR SEQ ID NO:7:

( i ) SEQUENCE CHARACTERISTICS:
        ( A ) LENGTH: 177 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
        Met  Phe  His  Val  Ser  Phe  Arg  Tyr  Ile  Phe  Gly  Leu  Pro  Pro  Leu  Ile
        1                   5                        10                       15

Leu  Val  Leu  Leu  Pro  Val  Ala  Ser  Ser  Asp  Cys  Asp  Ile  Glu  Gly  Lys
                            20                       25                       30

Asp  Gly  Lys  Gln  Tyr  Glu  Ser  Val  Leu  Met  Val  Ser  Ile  Asp  Gln  Leu
                       35                       40                       45

Leu  Asp  Ser  Met  Lys  Glu  Ile  Gly  Ser  Asn  Cys  Leu  Asn  Asn  Glu  Phe
                  50                       55                  60

Asn  Phe  Phe  Lys  Arg  His  Ile  Cys  Asp  Ala  Asn  Lys  Glu  Gly  Met  Phe
        65                            70                  75                       80

Leu  Phe  Arg  Ala  Ala  Arg  Lys  Leu  Arg  Gln  Phe  Leu  Lys  Met  Asn  Ser
                            85                       90                       95

Thr  Gly  Asp  Phe  Asp  Leu  His  Leu  Leu  Lys  Val  Ser  Glu  Gly  Thr  Thr
                       100                      105                      110

Ile  Leu  Leu  Asn  Cys  Thr  Gly  Gln  Val  Lys  Gly  Arg  Lys  Pro  Ala  Ala
                       115                      120                      125

Leu  Gly  Glu  Ala  Gln  Pro  Thr  Lys  Ser  Leu  Glu  Glu  Asn  Lys  Ser  Leu
                       130                      135                      140
```

```
Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

( 2 ) INFORMATION FOR SEQ ID NO:8:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Met Leu Leu Ala Met Val Leu Thr Ser Ala Leu Leu Cys Ser Val
1               5                   10                  15

Ala Gly Gln Gly Cys Pro Thr Leu Ala Gly Ile Leu Asp Ile Asn Phe
            20                  25                  30

Leu Ile Asn Lys Met Gln Glu Asp Pro Ala Ser Lys Cys His Cys Ser
            35                  40                  45

Ala Asn Val Thr Ser Cys Leu Cys Leu Gly Ile Pro Ser Asp Asn Cys
        50                  55                  60

Thr Arg Pro Cys Phe Ser Glu Arg Leu Ser Gln Met Thr Asn Thr Thr
65                  70                  75                  80

Met Gln Thr Arg Tyr Pro Leu Ile Phe Ser Arg Val Lys Lys Ser Val
                85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140
```

( 2 ) INFORMATION FOR SEQ ID NO:9:

( i ) SEQUENCE CHARACTERISTICS:
        ( A ) LENGTH: 162 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Met Arg Ile Ser Lys Pro His Leu Arg Ser Ile Ser Ile Gln Cys Tyr
1               5                   10                  15

Leu Cys Leu Leu Leu Lys Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95
```

```
       Val   Ile   Ser   His   Glu   Ser   Gly   Asp   Thr   Asp   Ile   His   Asp   Thr   Val   Glu
                         100                     105                     110

Asn   Leu   Ile   Ile   Leu   Ala   Asn   Asn   Ile   Leu   Ser   Ser   Asn   Gly   Asn   Ile
                   115                           120                     125

Thr   Glu   Ser   Gly   Cys   Lys   Glu   Cys   Glu   Glu   Leu   Glu   Glu   Lys   Asn   Ile
             130                           135                     140

Lys   Glu   Phe   Leu   Gln   Ser   Phe   Val   His   Ile   Val   Gln   Met   Phe   Ile   Asn
       145                           150                     155                                 160

Thr   Ser
```

( 2 ) INFORMATION FOR SEQ ID NO:10:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
       Met   Trp   Leu   Gln   Asn   Leu   Leu   Phe   Leu   Gly   Ile   Val   Val   Tyr   Ser   Leu
       1                       5                             10                          15

Ser   Ala   Pro   Thr   Arg   Ser   Pro   Ile   Thr   Val   Thr   Arg   Pro   Trp   Lys   His
                         20                          25                          30

Val   Glu   Ala   Ile   Lys   Glu   Ala   Leu   Asn   Leu   Leu   Asp   Asp   Met   Pro   Val
                   35                          40                          45

Thr   Leu   Asn   Glu   Glu   Val   Glu   Val   Val   Ser   Asn   Glu   Phe   Ser   Phe   Lys
             50                          55                          60

Lys   Leu   Thr   Cys   Val   Gln   Thr   Arg   Leu   Lys   Ile   Phe   Glu   Gln   Gly   Leu
       65                          70                          75                                80

Arg   Gly   Asn   Phe   Thr   Lys   Leu   Lys   Gly   Ala   Leu   Asn   Met   Thr   Ala   Ser
                         85                          90                          95

Tyr   Tyr   Gln   Thr   Tyr   Cys   Pro   Pro   Thr   Pro   Glu   Thr   Asp   Cys   Glu   Thr
                         100                         105                         110

Gln   Val   Thr   Thr   Tyr   Ala   Asp   Phe   Ile   Asp   Ser   Leu   Lys   Thr   Phe   Leu
                   115                         120                         125

Thr   Asp   Ile   Pro   Phe   Glu   Cys   Lys   Lys   Pro   Ser   Gln   Lys
             130                         135                         140
```

( 2 ) INFORMATION FOR SEQ ID NO:11:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
       Met   Trp   Leu   Gln   Ser   Leu   Leu   Leu   Leu   Gly   Thr   Val   Ala   Cys   Ser   Ile
       1                       5                             10                          15

Ser   Ala   Pro   Ala   Arg   Ser   Pro   Ser   Pro   Ser   Thr   Gln   Pro   Trp   Glu   His
                         20                          25                          30

Val   Asn   Ala   Ile   Gln   Glu   Ala   Arg   Arg   Leu   Leu   Asn   Leu   Ser   Arg   Asp
                   35                          40                          45

Thr   Ala   Ala   Glu   Met   Asn   Glu   Thr   Val   Glu   Val   Ile   Ser   Glu   Met   Phe
             50                          55                          60

Asp   Leu   Gln   Glu   Pro   Thr   Cys   Leu   Gln   Thr   Arg   Leu   Glu   Leu   Tyr   Lys
```

5,696,234

31

-continued

|   | 65 |   |   |   | 70 |   |   |   | 75 |   |   |   | 80 |
|---|---|---|---|---|---|---|---|---|---|---|---|---|---|
| Gln | Gly | Leu | Arg | Gly | Ser | Leu | Thr | Lys | Leu | Lys | Gly | Pro | Leu | Thr | Met |
|  |  |  |  | 85 |  |  |  |  | 90 |  |  |  |  | 95 |  |
| Met | Ala | Ser | His | Tyr | Lys | Gln | His | Cys | Pro | Pro | Thr | Pro | Glu | Thr | Ser |
|  |  |  | 100 |  |  |  |  | 105 |  |  |  |  | 110 |  |  |
| Cys | Ala | Thr | Gln | Ile | Ile | Thr | Phe | Glu | Ser | Phe | Lys | Glu | Asn | Leu | Lys |
|  |  | 115 |  |  |  |  | 120 |  |  |  |  | 125 |  |  |  |
| Asp | Phe | Leu | Leu | Val | Ile | Pro | Phe | Asp | Cys | Trp | Glu | Pro | Val | Gln | Glu |
|  | 130 |  |  |  |  | 135 |  |  |  |  | 140 |  |  |  |  |

( 2 ) INFORMATION FOR SEQ ID NO:12:

( i ) SEQUENCE CHARACTERISTICS:
      ( A ) LENGTH: 152 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:12:

| Met | Ser | Arg | Leu | Pro | Val | Leu | Leu | Leu | Gln | Leu | Leu | Val | Arg | Pro |
|---|---|---|---|---|---|---|---|---|---|---|---|---|---|---|
| 1 |  |  |  | 5 |  |  |  |  | 10 |  |  |  |  | 15 |
| Gly | Leu | Gln | Ala | Pro | Met | Thr | Gln | Thr | Thr | Ser | Leu | Lys | Thr | Ser | Trp |
|  |  |  | 20 |  |  |  |  | 25 |  |  |  |  | 30 |  |  |
| Val | Asn | Cys | Ser | Asn | Met | Ile | Asp | Glu | Ile | Ile | Thr | His | Leu | Lys | Gln |
|  |  | 35 |  |  |  |  | 40 |  |  |  |  | 45 |  |  |  |
| Pro | Pro | Leu | Pro | Leu | Leu | Asp | Phe | Asn | Asn | Leu | Asn | Gly | Glu | Asp | Gln |
|  | 50 |  |  |  |  | 55 |  |  |  |  | 60 |  |  |  |  |
| Asp | Ile | Leu | Met | Glu | Asn | Asn | Leu | Arg | Arg | Pro | Asn | Leu | Glu | Ala | Phe |
| 65 |  |  |  |  | 70 |  |  |  |  | 75 |  |  |  |  | 80 |
| Asn | Arg | Ala | Val | Lys | Ser | Leu | Gln | Asn | Ala | Ser | Ala | Ile | Glu | Ser | Ile |
|  |  |  |  | 85 |  |  |  |  | 90 |  |  |  |  | 95 |  |
| Leu | Lys | Asn | Leu | Leu | Pro | Cys | Leu | Pro | Leu | Ala | Thr | Ala | Ala | Pro | Thr |
|  |  |  | 100 |  |  |  |  | 105 |  |  |  |  | 110 |  |  |
| Arg | His | Pro | Ile | His | Ile | Lys | Asp | Gly | Asp | Trp | Asn | Glu | Phe | Arg | Arg |
|  |  | 115 |  |  |  |  | 120 |  |  |  |  | 125 |  |  |  |
| Lys | Leu | Thr | Phe | Tyr | Leu | Lys | Thr | Leu | Glu | Asn | Ala | Gln | Ala | Gln | Gln |
|  | 130 |  |  |  |  | 135 |  |  |  |  | 140 |  |  |  |  |
| Thr | Thr | Leu | Ser | Leu | Ala | Ile | Phe |  |  |  |  |  |  |  |  |
| 145 |  |  |  |  | 150 |  |  |  |  |  |  |  |  |  |  |

( 2 ) INFORMATION FOR SEQ ID NO:13:

( i ) SEQUENCE CHARACTERISTICS:
      ( A ) LENGTH: 134 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

| Met | Arg | Met | Leu | Leu | His | Leu | Ser | Leu | Leu | Ala | Leu | Gly | Ala | Ala | Tyr |
|---|---|---|---|---|---|---|---|---|---|---|---|---|---|---|---|
| 1 |  |  |  | 5 |  |  |  |  | 10 |  |  |  |  | 15 |  |
| Val | Tyr | Ala | Ile | Pro | Thr | Glu | Ile | Pro | Thr | Ser | Ala | Leu | Val | Lys | Glu |
|  |  |  | 20 |  |  |  |  | 25 |  |  |  |  | 30 |  |  |
| Thr | Leu | Ala | Leu | Leu | Ser | Thr | His | Arg | Thr | Leu | Leu | Ile | Ala | Asn | Glu |
|  |  | 35 |  |  |  |  | 40 |  |  |  |  | 45 |  |  |  |
| Thr | Leu | Arg | Ile | Pro | Val | Pro | Val | His | Lys | Asn | His | Gln | Leu | Cys | Thr |

-continued

|   |   |   |   |   | 50 |   |   |   |   | 55 |   |   |   |   | 60 |   |   |   |   |
|---|---|---|---|---|---|---|---|---|---|---|---|---|---|---|---|---|---|---|---|

Glu Glu Ile Phe Gln Gly Ile Gly Thr Leu Glu Ser Gln Thr Val Gln
65                    70                    75                    80

Gly Gly Thr Val Glu Arg Leu Phe Lys Asn Leu Ser Leu Ile Lys Lys
                  85                    90                    95

Tyr Ile Asp Gly Gln Lys Lys Lys Cys Gly Glu Glu Arg Arg Arg Val
              100                   105                   110

Asn Gln Phe Leu Asp Tyr Leu Gln Glu Phe Leu Gly Val Met Asn Thr
          115                   120                   125

Glu Trp Ile Ile Glu Ser
      130

(2) INFORMATION FOR SEQ ID NO:14:

(i) SEQUENCE CHARACTERISTICS:
      (A) LENGTH: 112 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:14:

Gly Pro Val Pro Pro Ser Thr Ala Leu Arg Lys Leu Ile Glu Glu Leu
1               5                    10                   15

Val Asn Ile Thr Gln Asn Gln Lys Ala Pro Leu Cys Asn Gly Ser Met
              20                    25                   30

Val Trp Ser Ile Asn Leu Thr Ala Gly Met Tyr Cys Ala Ala Leu Glu
          35                    40                   45

Ser Leu Ile Asn Val Ser Gly Cys Ser Ala Ile Glu Lys Thr Gln Asp
      50                    55                   60

Met Leu Ser Gly Phe Cys Pro His Lys Val Ser Ala Gly Gln Phe Ser
65                    70                    75                   80

Ser Leu His Val Arg Asp Thr Lys Ile Glu Val Ala Gln Phe Val Lys
              85                    90                   95

Asp Leu Leu Leu His Leu Lys Lys Leu Phe Arg Glu Gly Arg Phe Asn
          100                   105                  110

(2) INFORMATION FOR SEQ ID NO:15:

(i) SEQUENCE CHARACTERISTICS:
      (A) LENGTH: 111 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:15:

Gly Pro Val Pro Pro Ser Thr Ala Leu Arg Lys Leu Ile Glu Glu Leu
1               5                    10                   15

Val Asn Ile Thr Gln Asn Gln Lys Ala Pro Leu Cys Asn Gly Ser Met
              20                    25                   30

Val Trp Ser Ile Asn Leu Thr Ala Gly Met Tyr Cys Ala Ala Leu Glu
          35                    40                   45

Ser Leu Ile Asn Val Ser Gly Cys Ser Ala Ile Glu Lys Thr Gln Asp
      50                    55                   60

Met Leu Ser Gly Phe Cys Pro His Lys Val Ser Ala Gly Phe Ser Ser
65                    70                    75                   80

Leu His Val Arg Asp Thr Lys Ile Glu Val Ala Gln Phe Val Lys Asp

-continued

```
                            85                           90                             95
         Leu  Leu  Leu  His  Leu  Lys  Lys  Leu  Phe  Arg  Glu  Gly  Arg  Phe  Asn
                        100                      105                      110
```

(2) INFORMATION FOR SEQ ID NO:16:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Gly  Pro  Val  Pro  Arg  Ser  Val  Ser  Leu  Pro  Leu  Thr  Leu  Lys  Glu  Leu
  1                  5                        10                       15

Ile  Glu  Glu  Leu  Ser  Asn  Ile  Thr  Gln  Asp  Glu  Thr  Pro  Leu  Cys  Asn
                20                       25                       30

Gly  Ser  Met  Val  Trp  Ser  Val  Asp  Leu  Ala  Ala  Gly  Gly  Phe  Cys  Val
            35                       40                  45

Ala  Leu  Asp  Ser  Leu  Thr  Asn  Ile  Ser  Asn  Cys  Asn  Ala  Ile  Tyr  Arg
       50                       55                  60

Thr  Gln  Asp  Ile  Leu  His  Gly  Leu  Cys  Asn  Arg  Lys  Ala  Pro  Thr  Thr
 65                       70                  75                           80

Val  Ser  Ser  Leu  Pro  Asp  Thr  Lys  Ile  Glu  Val  Ala  His  Phe  Ile  Thr
                 85                       90                           95

Lys  Leu  Leu  Ser  Tyr  Thr  Lys  Gln  Leu  Phe  Arg  His  Gly  Pro  Phe
                100                      105                      110
```